United States Patent [19]
Bowers

[11] Patent Number: 5,373,366
[45] Date of Patent: Dec. 13, 1994

[54] INK CONCENTRATION MEASURING AND CONTROL AND CONTROL CIRCUIT

[75] Inventor: Mark C. Bowers, Vandalia, Ohio

[73] Assignee: Scitex Digital Printing, Inc, Dayton, Ohio

[21] Appl. No.: 57,436

[22] Filed: May 4, 1993

Related U.S. Application Data

[63] Continuation-in-part of Ser. No. 796,191, Nov. 22, 1991, abandoned.

[51] Int. Cl.$^5$ .............................................. G01N 21/59
[52] U.S. Cl. ..................................... 356/435; 356/436
[58] Field of Search ............... 356/432, 433, 435, 436, 356/440, 442; 250/573

[56] References Cited

U.S. PATENT DOCUMENTS

| | | | |
|---|---|---|---|
| 3,743,430 | 7/1973 | Riggs | 356/435 |
| 4,224,405 | 9/1980 | Hijikata | 356/436 |
| 4,337,468 | 6/1982 | Mizuno | 346/1.1 |
| 4,776,693 | 10/1988 | Imamura et al. | 356/243 |
| 5,241,189 | 8/1993 | Vandagriff et al. | 356/435 |

Primary Examiner—Richard A. Rosenberger
Attorney, Agent, or Firm—Barbara Joan Haushalter

[57] ABSTRACT

In an ink concentration measuring circuit, a light emitting diode emits light toward an ink cell. A first photo diode receives reflected light from the ink cell and provides a reference signal and a second photo diode receives direct light through the ink cell and provides an ink signal. A ratio of the reference signal to the ink signal is then calculated and used to determine a concentration of ink in the ink cell. Since changes in the ink temperature affect the ink concentration, the ink temperature may be measured and the result used to modify the ratio, compensating for the changes in ink temperature. Also, ink pressure may be measured and used to modify the ratio, compensating for changes in the dimensions of the ink cell.

13 Claims, 3 Drawing Sheets

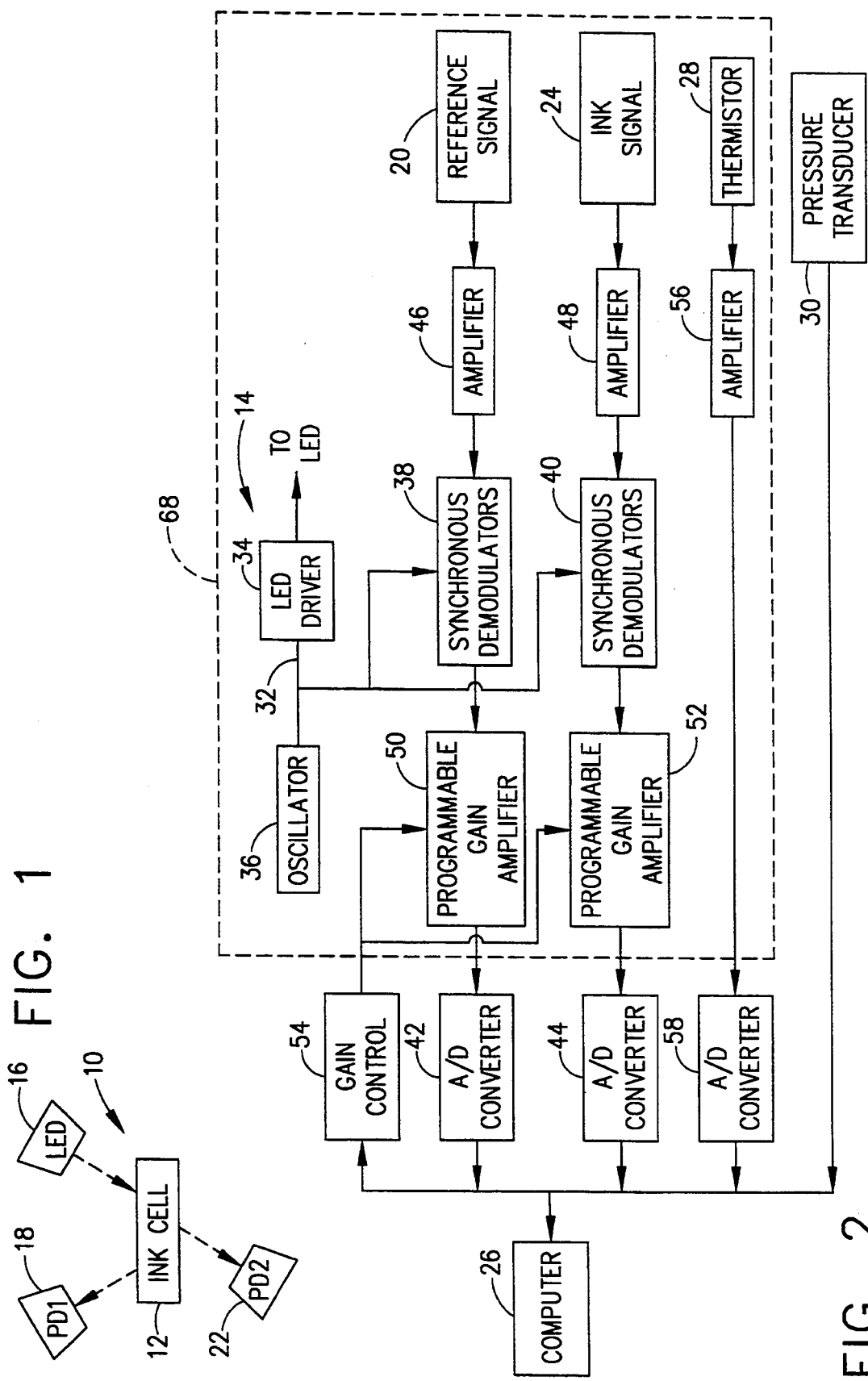

INK CONCENTRATION MEASURING AND CONTROL AND CONTROL CIRCUIT

This is a continuation of application Ser. No. 07/796,191, filed Nov. 22, 1991 now abandoned.

TECHNICAL FIELD

The present invention relates to ink output in ink jet printing systems and, more particularly, to an ink concentration measuring circuit for controlling the concentration of the ink output.

BACKGROUND ART

Ink concentration as measured by an ink cell, used in optical concentration measurement devices, affects the ink jet printing process. As the ink concentration varies, the optimal parameters used to control the ink jet printing process change as a function of the ink concentration. Currently, a variety of methods exist for calibrating optical concentration assemblies in order to determine ink concentration effects. For example, a typical optical concentration device includes a light source which directs a path of light toward an ink cell. A photo diode is situated such that the ink cell is between the light source and the photo diode. The light from the light source is first measured with the ink cell in place, such that the light received by the photo diode is filtered through the ink cell. The ink cell is then moved out of the light path, so the light from the light source shines directly on the photo diode. A comparison between the light received through the ink cell and directly with the ink cell removed is made to calibrate the optical concentration device. However, it is a time consuming process to have to continually move the ink cell in order to update calibrations.

Alternatively, then, calibration can be accomplished manually, without moving the ink cell. In this instance, a known reference, such as ink quality in the ink cell, is used to manually calibrate a light source, such as an LED, output to some nominal value. The LED light is directed through the ink of known quality toward a photo diode, and the light output to the photo diode is used to determine the LED output. This method, however, ignores the effects of temperature drift. Since absorption, which increases exponentially with concentration, varies with ink temperature, it is important to be able to compensate for temperature drift so that the ink concentration can be controlled. Additionally, ink pressure affects the dimensions of relatively inexpensive ink cells, affecting the ink concentration measurement. Unfortunately, ink cells which are less susceptible to pressure changes are also more expensive. Finally, in known methods of ink concentration measurements, the ink cell is required to be placed very close to the measuring circuitry to avoid noise problems.

It is seen then that there exists a need for an ink concentration measuring circuit which accounts for variables which affect ink concentration, including ink temperature and ink pressure.

SUMMARY OF THE INVENTION

This need is met by the system according to the present invention, wherein an ink concentration measuring circuit measures ink temperature and ink pressure to compensate for changes in the ink concentration caused by these variables.

In accordance with one aspect of the present invention, an ink concentration measurement and control circuit comprises a light emitting diode for emitting light toward an ink cell. A first photo diode receives reflected light from the ink cell and provides a reference signal and a second photo diode receives direct light through the ink cell and provides an ink signal. A ratio of the reference signal to the ink signal is calculated and a concentration of ink in the ink cell is then calculated, based on the ratio. The ink concentration measuring circuit may further include a means for measuring ink temperature to modify the ratio to compensate for changes in the ink temperature. Finally, the ink concentration measuring circuit may include a means for measuring ink pressure to modify the ratio to compensate for changes in dimensions of the ink cell.

The present invention also provides for a method of measuring the ink concentration in an ink cell including the step of emitting light toward the ink cell. The method further includes the steps of positioning a first photo diode for receiving reflected light from the ink cell and providing a reference signal and positioning a second photo diode for receiving direct light through the ink cell and providing an ink signal. Finally, the method comprises the steps of calculating a ratio of the reference signal to the ink signal and determining a concentration of ink in the ink cell based on the ratio. The method may also comprise the steps of measuring ink temperature and modifying the ratio to compensate for changes in the ink temperature and measuring ink pressure and modifying the ratio to compensate for changes in dimensions of the ink cell.

Accordingly, it is an object of the present invention to provide an inexpensive, yet accurate ink concentration measuring circuit. It is an advantage of the present invention that variables affecting the ink concentration measurement are measured, and the ink concentration measurement adjusted accordingly. Finally, the ink concentration can also be adjusted to achieve a desired ink concentration.

Other objects and advantages of the invention will be apparent from the following description, the accompanying drawings and the appended claims.

BRIEF DESCRIPTION OF THE DRAWINGS

FIG. 1 is an optical concentration assembly in accordance with the present invention;

FIG. 2 is a block diagram of the ink concentration measuring circuit of the present invention;

DETAILED DESCRIPTION OF THE PREFERRED EMBODIMENTS

Figure 3:
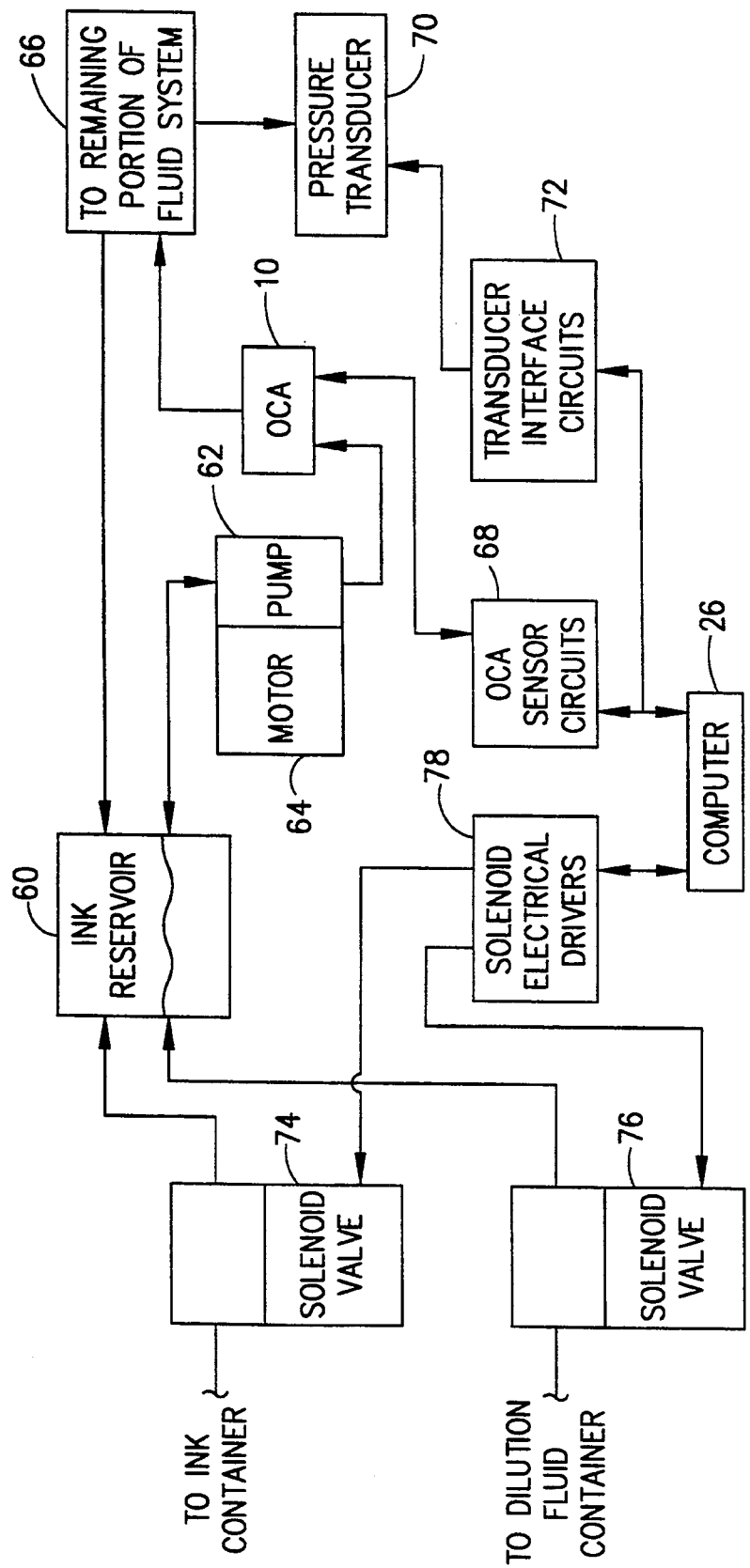
FIG. 3 a schematic block diagram of the physical components of the ink concentration control process for the ink concentration assembly of FIG. 1.

The present invention provides for an ink concentration measurement and control circuit for sensing and controlling the concentration of ink output, or the ink concentration of an ink cell. An ink of known quality is put into the ink cell of an optical concentration assembly. A computer, connected to an ink concentration measuring circuit, reads signal values from first and second photo diodes through analog to digital converters. The computer then determines a ratio of a reference signal, provided by the first photo diode, to an ink signal, provided by the second photo diode. This ratio is used to determine the ink concentration and whether the ink in the ink cell is higher or lower than the desired concentration. If the ink concentration is too high, a dilutant may be added to dilute the fluid in the ink cell. Alternatively, if the ink concentration is too low, ink may be added to the fluid. Finally, the computer can adjust a gain, ultimately adjusting the ratio to approach the desired concentration.

With the present invention, the calculation of the actual ink concentration from the OCA ratio is unnecessary, since the OCA ratio is only a number that is proportional to a concentration value expressed in standard measurement units, and not a scientific unit of measure. The measured OCA ratio is compared to a target or threshold OCA ratio, for example 100% concentration. A concentration differing from the threshold determines the selection of the type and amount of replenishment fluid. For example, ink is selected as the replenishment fluid when the ratio exceeds the ratio nominal for the desired concentration, and dilution fluid is selected as the replenishment fluid when the ratio is less than the ratio nominal for the desired concentration.

Referring now to the drawings, in FIG. 1 there is illustrated an optical concentration assembly (OCA) 10 including an ink cell 12 having an ink concentration. The ink concentration of the ink cell 12 is measured using the ink concentration measuring circuit 14 of FIG. 2. Ill the OCA 10, light is emitted from a light source, such as a light emitting diode (LED) 16, toward the ink cell 12. The particular LED used is chosen based on the spectral characteristic needed for the particular application, and is commercially available.

Continuing with FIG. 1, a first photo diode 18 receives light reflected from the ink cell 12 and provides a reference signal 20. Similarly, a second photo diode 22 receives light directly through the ink cell 12 and provides an ink signal 24. Obviously, the ink concentration in the ink cell 12 will affect the amount of light that is both reflected from and directed through the ink cell 12. Hence, a ratio of the reference signal to the ink signal is calculated and used to determine the concentration of ink in the ink cell 12. The ratio can also be used as a target to determine if the ink concentration is higher or lower than a desired ink concentration, since for any given ink concentration the ratio of the reference signal 20 to the ink signal 24 remains constant.

Referring now to FIG. 2, the ink concentration measuring circuit 14 may store each determined ratio in a permanent memory of a computer 26 for future reference. There is no direct calibration of the circuit 14 required, as calibration is accomplished during manufacture. The ink concentration measuring circuit 14 is used for outputting voltage signals indicative of the magnitude of the reference signal 20, the magnitude of the ink signal 24, the temperature of the ink from a temperature sensing device such as a thermistor 28, and the pressure of the ink from a pressure sensing device such as a pressure transducer 30. A square wave signal along line 32 is used applied to an LED driver 34 to turn the LED 16 of the OCA 10 on and off. The square wave signal is preferably at a standard 50% duty cycle and 5 KHz rate, from an oscillator 36. Since the present invention uses a square wave, the spectral content of the output of the photo diodes 18 and 22 is greater at the fundamental frequency of 5 KHz than if a narrow pulse is used. This feature allows the design of first and second synchronous demodulators 38 and 40, which also receive the 5 KHz signal from the oscillator 36, to have a relatively narrow signal bandpass response. This design, therefore, permits the ink cell 12 to be situated remote from the circuit 14, minimizing 60 Hertz and harmonics noise as well as other noise which affect the photo diodes 18 and 22.

The computer 26 reads the reference signal 20 and the ink signal 24 through analog to digital converters 42 and 44, respectively. Initially, however, the reference signal 20 and the ink signal 24 are amplified at amplifiers 46 and 48, respectively, before being demodulated at the synchronous demodulators 38 and 40. The amplifiers 46 and 48 are, in effect, operating as chopper stabilization amplifiers. An advantage of having amplifiers 46 and 48 and synchronous demodulators 38 and 40, is the minimization of temperature drift in the circuit 14 and the minimization of stray noise pick-up, including ambient noise.

Continuing with FIG. 2, the demodulated signals from synchronous demodulators 38 and 40 are provided to programmable gain amplifiers 50 and 52, respectively, before being output to the analog-to-digital converters 42 and 44, respectively. The computer 26 then divides the resulting ink voltage from the analog-to-digital converter 42 by the resulting reference voltage from analog-to-digital converter 44, to produce a ratio which is representative of the ink concentration of the ink cell 12. The ratio tells the computer 26 if the ink concentration is higher or lower than the desired concentration. Based on this ratio, the computer 26 can adjust the fluid concentration by adding an ink mixture or a concentration reducing mixture. The computer 26 also has the option of setting its operating parameters. For example, the computer can adjust the reference voltage and the ink voltage, using a gain control 54 to increase or decrease the programmable gain amplifiers 50 and 52, altering and amplifying the gain simultaneously. Since, for any given ink concentration, the ratio of the reference signal 20 to the ink signal 24 remains the same, the ratios stored in the permanent memory of the computer 26 may be used for a look-up table to adjust the ratio to approach and achieve the desired ink concentration.

Referring now to FIG. 3, the physical components of the ink concentration control process are illustrated in schematic block diagram form. During normal operation, there is ink flow from an ink reservoir 60 to an ink pump 62, associated with a motor 64, which in turn supplies ink under pressure to the OCA 10 and the remaining portion of the fluid system, indicated by block 66. The OCA 10 receives only ink, and not an ink/air mixture. As disclosed above in reference to FIG. 1, the OCA comprises the LED 16 and the two photo sensitive sensors 18 and 22. One photo diode 18 registers the light reflected by the cell 12 top surface, and the other photo diode 22 registers the light through the ink filled cell 12. This ink concentration information is received by the computer 26 through OCA sensor circuit 68, shown by the dotted line of block 68 in FIG. 2.

Thermistor 28 is mounted in the assembly 10 to measure the temperature of the ink in the assembly. Ink pressure is measured by pressure transducer 70, via transducer interface circuitry 72, at a point which is known to have a fixed relationship to the pressure at the OCA. The computer also receives ink fluid and dilution fluid information from solenoid valves 74 and 76, respectively, via solenoid electrical drivers 78. The computer 26 reads all of these parameters and makes the calculation of the ink concentration with respect to predicted parameters that would be present if 100% concentration ink were being used.

If the calculation of the measured value is less than or equal to the predicted values of 100% concentration ink, an indication that the ink being used to print is diluted, the solenoid valve 74 which controls refill of the ink container is activated whenever the ink level in the ink reservoir 60 allows replacement of the consumed ink. If the calculation of the measured value is greater than the predicted value of 100% concentration ink, an indication that the ink being used to print is too concentrated, the solenoid valve 76 which controls refill of the dilution fluid container is activated whenever the ink level in the ink reservoir 60 allows replacement of the consumed dilutant. This can be represented by the following equation:

$$OCA\ ratio = \frac{Ink\ Sensor\ Response}{Reference\ Sensor\ Response} \times K(p,\ t)$$

where $K(p,t,)$ is a correction factor as a function of pressure (p) and temperature (t); and the reference sensor response is provided by the first photo diode 18, and the ink sensor response is provided by the second photo diode 22, which provide reference signal 20 and ink signal 24, respectively, based on the ink characteristics. The correction factor can be a calculated formula or a lookup table in the memory of the computer 26. Alternatively, a precalculated set of OCA ratios for 100% concentration ink, with pressure and temperature as variables, can be stored in the memory of the computer 26 and then compared to the measured calculated OCA ratio. The comparison of the measured OCA ratio to the predicted 100% concentration OCA ratio determines which refill fluid is selected.

Figure 4:
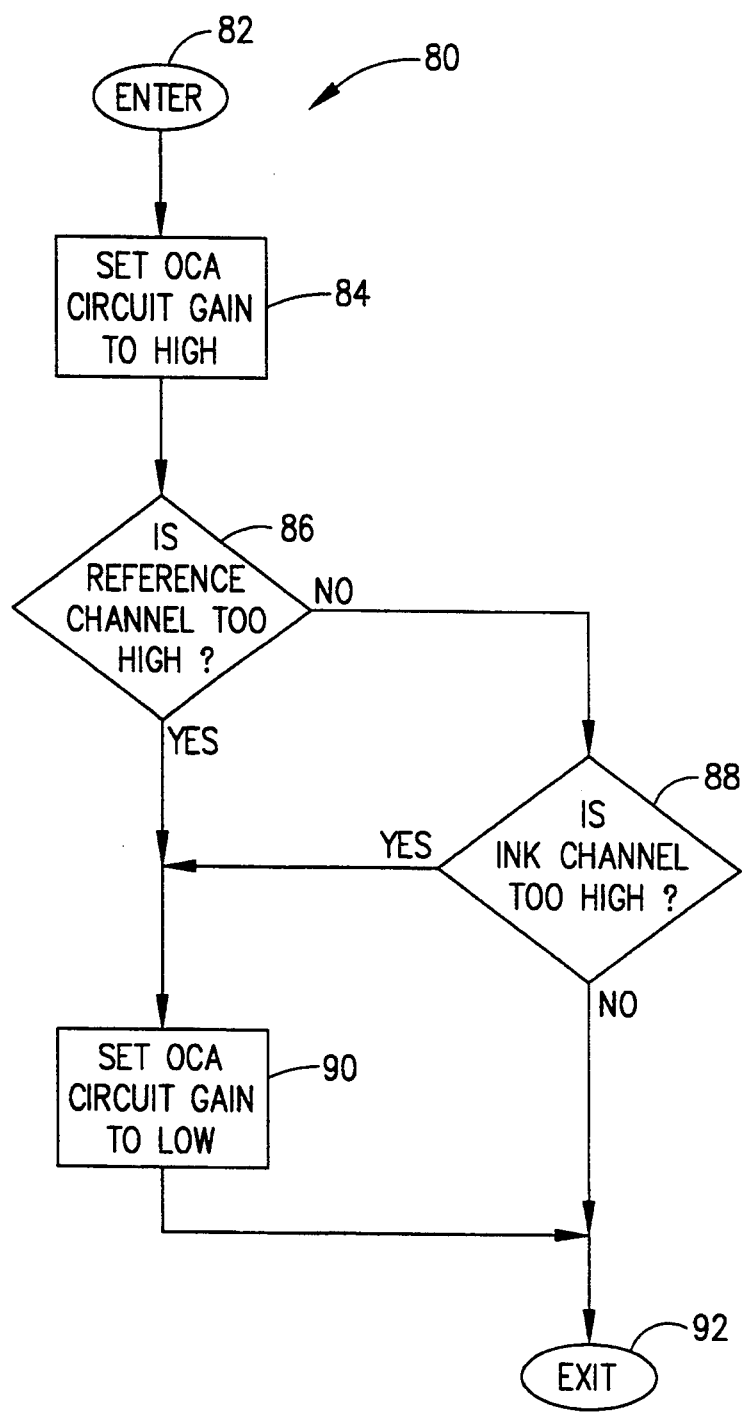
FIG. 4 is a flow diagram illustrating the steps for selecting the gain of the optical concentration assembly circuit of FIG. 1.

Referring now to FIG. 4, a flow diagram 80 for selecting the gain of the OCA circuit 10 is illustrated. Gain adjustment is provided for tolerance of components and also for adaptation of different inks, which have different optical characteristics. The computer 26 controls the ink concentration by controlling adjustment of the ink mixture or the concentration reducing mixture. This, in turn, alters the characteristics of the ink cell 12, thereby creating a closed loop effect for ink concentration control. The computer 26, then, selects the gain of the programmable gain amplifiers, to control the ink concentration in the cell 12.

Variations in the LED 16 output level presents a tolerancing problem for the selection of the gain of the photo sensor amplifier stages of elements 38, 40, 46, 48, 50, and 52. As illustrated in the flow diagram 80 of FIG. 4, the program starts at block 82 and proceeds to block 84, where the computer 26 sets the OCA circuit 10 to a high gain. That is, both the reference channel amplifier 50 and the ink channel sensor amplifier 52 are both set to high gain. If either channel has an output which is above a set limit, as determined at decision blocks 86 and 88, the gain of both channels is set to low gain at block 90, such as one-half gain. This insures that the output of both channels are well within the nominal operation range of the computer's analog to digital (A/D) converter. For example, if the A/D converter has an input operating range of 0 to 5 volts, it is preferred that its input not be allowed to be nominally 4.8 volts. A more ideal nominal voltage is half that amount, or 2.4 volts. Beyond the initial tolerancing of the LED's output, as the LED heats up or ages, its output changes. But the effect is canceled out by the gain adjustment and the calculation of the OCA ratio value. It should be noted that this feature can be extended to any value of gain selections, so long as the gain of both channels are altered by the same factor, since the OCA ratio calculation and the equal gain change of each channel cancels out variations. The program then exits at block 92.

Since the ink concentration measurement is affected by temperature, a temperature signal from thermistor 28 of FIG. 2 may also be provided to the computer 26. The temperature signal is amplified at amplifier 56 to output an ink temperature voltage to an analog-to-digital converter 58. The ink temperature voltage from the analog-to-digital converter 58 is then provided to the computer 26. The computer 26 is then capable of using look up tables in order to modify the ratio appropriately, to eliminate the effect of the temperature on the ink concentration.

Similarly, since the ink concentration is affected by ink pressure, the pressure transducer 30 may be included in the circuit 14. The pressure transducer 30 is capable of generating a pressure signal indicative of the pressure of the ink from the fluid in the OCA 10. The pressure transducer 30 may include a pressure sensing element or other suitable means for detecting pressure and producing a related signal to be provided to the computer 26. The computer 26 can then compensate for changes in dimensions of the ink cell 12 caused by changes in the ink pressure when adjusting the ratio to achieve the desired ink concentration.

The present invention provides for a system and a method of measuring the ink concentration in an ink cell. The ink concentration measuring circuit outputs voltage signals indicative of the magnitude of the reference channel, the magnitude of the ink channel, the temperature of the ink, and the pressure of the ink. These values are then used to adjust the ink concentration in order to achieve a desired ink concentration.

Having described the invention in detail and by reference to the preferred embodiment thereof, it will be apparent that other modifications and variations are possible without departing from the scope of the invention defined in the appended claims.

What is claimed is:

1. An ink concentration measuring and control system comprising:
    a light source for emitting light toward an ink cell;
    a first photo diode for receiving reflected light from said ink cell and providing a reference signal;
    a second photo diode for receiving direct light through said ink cell and providing an ink signal;
    means for calculating a ratio of said reference signal to said ink signal;
    means for measuring ink pressure to modify said ratio to compensate for changes in dimensions of said ink cell; and
    means for controlling a concentration of ink in said ink cell based on said ratio.

2. An ink concentration measuring and control system as claimed in 1 wherein the means for controlling a concentration of ink comprises:
    means for determining when the said ratio differs from a ratio nominal for a desired concentration; and
    means for providing a replenishment fluid when said ratio differs from the ratio nominal for the desired concentration.

3. An ink concentration measuring and control system as claimed in claim 2 wherein ink is selected as the replenishment fluid when said ratio exceeds the ratio nominal for the desired concentration.

4. An ink concentration measuring and control system as claimed in claim 2 wherein dilution fluid is selected as the replenishment fluid when said ratio is less than the ratio nominal for the desired concentration.

5. An ink concentration measuring and control system as claimed in claim 1 further comprising means for measuring ink temperature to modify said ratio to compensate for changes in said ink temperature.

6. An ink concentration measuring and control system as claimed in claim 1 wherein said light source is a light emitting diode.

7. An ink concentration measuring and control system as claimed in claim 1 further comprising a means for adjusting said ratio to achieve a desired ratio.

8. An ink concentration measuring and control system as claimed in claim 7 wherein said means for adjusting said ratio comprises a computer gain control.

9. A method of measuring and controlling ink concentration comprising the steps of:

emitting light toward an ink cell;

positioning a first photo diode for receiving reflected light from said ink cell and providing a reference signal;

positioning a second photo diode for receiving direct light through said ink cell and providing an ink signal;

calculating a ratio of said reference signal to said ink signal;

measuring ink pressure to modify said ratio to compensate for changes in dimensions of said ink cell; and controlling a concentration of ink in said ink cell based on said ratio.

10. A method as claimed in claim 9 further comprising the step of measuring ink temperature to modify said ratio to compensate for changes in said ink temperature.

11. A method as claimed in claim 9 wherein said step of emitting light toward an ink cell further comprises the step of providing a light emitting diode for emitting light.

12. A method as claimed in claim 9 further comprising the step of adjusting said ratio to achieve a desired ratio.

13. A method as claimed in claim 12 wherein said step of adjusting said ratio further comprises the step of providing a computer gain control for adjusting said ratio.

* * * * *